United States Patent
McLaughlin (10) Patent No.: US 11,517,658 B2
(45) Date of Patent: Dec. 6, 2022

(54) DEVICES, SYSTEMS, AND METHODS OF PACKAGING FOR A PRE-FILLED DRUG DELIVERY DEVICE

(71) Applicant: Insulet Corporation, Acton, MA (US)

(72) Inventor: Ian McLaughlin, Groton, MA (US)

(73) Assignee: INSULET CORPORATION, Acton, MA (US)

( * ) Notice: Subject to any disclaimer, the term of this patent is extended or adjusted under 35 U.S.C. 154(b) by 360 days.

(21) Appl. No.: 16/897,988

(22) Filed: Jun. 10, 2020

(65) Prior Publication Data

US 2020/0297920 A1 Sep. 24, 2020

Related U.S. Application Data (62) Division of application No. 16/053,227, filed on Aug. 2, 2018, now Pat. No. 10,722,640.

(Continued)

(51) Int. Cl.
*A61L 2/20* (2006.01)
*A61M 5/00* (2006.01)
(Continued)

(52) U.S. Cl.
CPC ........... *A61M 5/001* (2013.01); *A61L 2/0094* (2013.01); *A61L 2/206* (2013.01); *A61M 5/002* (2013.01);
(Continued)

(58) Field of Classification Search
CPC .... A61L 2/0023; A61L 2/0035; A61L 2/0082; A61L 2/0094; A61L 2/07; A61L 2/20;
(Continued)

(56) References Cited

U.S. PATENT DOCUMENTS 2,833,007 A 5/1958 Messer et al.
4,307,713 A 12/1981 Galkin et al.
(Continued)

FOREIGN PATENT DOCUMENTS

CN 1898131 A 1/2007
EP 2099384 A1 9/2009
(Continued)

OTHER PUBLICATIONS

International Search Report and Written Opinion for PCT/US18/52468, dated Feb. 26, 2019, 16 pages.

(Continued)

*Primary Examiner* — Timothy C Cleveland
(74) *Attorney, Agent, or Firm* — Goodwin Procter LLP (57) ABSTRACT

A system for sterilizing a drug delivery device includes a drug delivery device having a first self-healing seal configured to seal a fluid reservoir disposed within the drug delivery device. A sealable container is configured to receive the drug delivery device therein. The sealable container has a base portion and a cover portion. The cover portion has a second self-healing seal positioned to align with the first self-healing seal when the drug delivery device is disposed within the sealable container. A fill port includes a fill path, the fill path being configured to pass through the first and second self-healing seals to fluidly couple the fill port to the reservoir of the drug delivery device. Other systems, methods, and devices of sterilization are also disclosed.

21 Claims, 6 Drawing Sheets

Related U.S. Application Data (60) Provisional application No. 62/540,701, filed on Aug. 3, 2017.

(51) Int. Cl.
*A61M 5/31* (2006.01)
*A61L 2/00* (2006.01)
*B65B 3/04* (2006.01)
*A61M 5/142* (2006.01)

(52) U.S. Cl.
CPC ............ *A61M 5/3129* (2013.01); *B65B 3/04* (2013.01); *A61L 2202/182* (2013.01); *A61L 2202/21* (2013.01); *A61L 2202/23* (2013.01); *A61L 2202/24* (2013.01); *A61M 5/14248* (2013.01); *A61M 2005/312* (2013.01); *A61M 2005/3114* (2013.01); *A61M 2005/3128* (2013.01); *A61M 2005/3131* (2013.01); *A61M 2209/045* (2013.01)

(58) Field of Classification Search
CPC .. A61L 2/206; A61L 2202/21; A61L 2202/23; B65B 3/04
See application file for complete search history.

(56) References Cited

U.S. PATENT DOCUMENTS

| | | | |
|---|---|---|---|
| 4,416,663 A | 11/1983 | Hall | |
| 4,801,957 A | 1/1989 | Vandemoere | |
| 4,850,954 A | 7/1989 | Charvin | |
| 4,882,600 A | 11/1989 | Van de Moere | |
| 4,973,998 A | 11/1990 | Gates | |
| 5,045,871 A | 9/1991 | Reinholdson | |
| 5,239,326 A | 8/1993 | Takai | |
| 5,452,033 A | 9/1995 | Balling et al. | |
| 5,576,781 A | 11/1996 | Deleeuw | |
| 5,899,882 A | 5/1999 | Waksman et al. | |
| 6,164,044 A | 12/2000 | Porfano et al. | |
| 6,685,452 B2 | 2/2004 | Christiansen et al. | |
| 6,767,319 B2 | 7/2004 | Reilly et al. | |
| 7,182,726 B2 | 2/2007 | Williams et al. | |
| 7,303,073 B2 | 12/2007 | Raynal-Olive et al. | |
| 8,056,719 B2 | 11/2011 | Porret et al. | |
| 8,105,282 B2 | 1/2012 | Susi et al. | |
| 8,461,561 B2 | 6/2013 | Freeman et al. | |
| 8,727,117 B2 | 5/2014 | Maasarani | |
| 8,747,739 B2* | 6/2014 | Parker | A61B 50/00 422/294 |
| 9,005,166 B2 | 4/2015 | Uber, III et al. | |
| 9,248,229 B2 | 2/2016 | Devouassoux et al. | |
| 9,427,710 B2 | 8/2016 | Jansen | |
| 9,555,911 B2 | 1/2017 | Pawlowski et al. | |
| 9,598,195 B2 | 3/2017 | Deutschle et al. | |
| 9,862,519 B2 | 1/2018 | Deutschle et al. | |
| 10,086,131 B2 | 10/2018 | Okihara | |
| 10,342,926 B2 | 7/2019 | Nazzaro et al. | |
| 2004/0139698 A1 | 7/2004 | Grifols | |
| 2005/0133729 A1 | 6/2005 | Woodworth et al. | |
| 2005/0147527 A1* | 7/2005 | Brown | A61L 2/208 422/292 |
| 2005/0222539 A1 | 10/2005 | Gonzales et al. | |
| 2006/0086909 A1 | 4/2006 | Schaber | |
| 2009/0254041 A1 | 10/2009 | Krag et al. | |
| 2014/0163664 A1 | 6/2014 | Goldsmith | |
| 2015/0057613 A1 | 2/2015 | Clemente et al. | |
| 2015/0078961 A1 | 3/2015 | Opie | |
| 2015/0196720 A1 | 7/2015 | Okihara et al. | |
| 2016/0262984 A1 | 9/2016 | Arnott et al. | |
| 2017/0197028 A1 | 7/2017 | Goldsmith | |

FOREIGN PATENT DOCUMENTS

| | | |
|---|---|---|
| ES | 2559866 T3 | 2/2016 |
| GB | 2461086 A | 12/2009 |
| JP | H09010282 A | 1/1997 |
| JP | 2002126039 A | 5/2002 |
| JP | 2007516775 A | 6/2007 |
| WO | 2007039930 A1 | 4/2007 |
| WO | 2017089289 A1 | 6/2017 |
| WO | 2017205816 A1 | 11/2017 |
| WO | 2018075851 A2 | 4/2018 |

OTHER PUBLICATIONS

International Search Report and Written Opinion for PCT/US2017/061095, dated Feb. 20, 2018, 8 pages.

International Preliminary Report on Patentability for the International Patent Application No. PCT/US2017/061095, dated May 23, 2019, 7 pages.

* cited by examiner

DEVICES, SYSTEMS, AND METHODS OF PACKAGING FOR A PRE-FILLED DRUG DELIVERY DEVICE

CROSS-REFERENCE TO RELATED APPLICATIONS

This application is a division of U.S. application Ser. No. 16/053,227, filed Aug. 2, 2018, which claims the benefit of priority under 35 U.S.C. § 119 to U.S. Provisional Patent Application Ser. No. 62/540,701, filed Aug. 3, 2017, which the contents of both are incorporated by reference herein in their entirety.

TECHNICAL FIELD

The present application generally relates to medication delivery devices, and more particularly to systems and methods for providing pre-filled sterilized drug delivery devices.

BACKGROUND

Conventional drug delivery devices are often provided to a user without a liquid drug prefilled in a drug container of the device. The patient is therefore often required to fill the drug device prior to use. This sequence is implemented because it can be difficult to completely sterilize a device that is pre-filled with the drug without damaging the drug. Conventional sterilization processes may require heat, radiation, or chemicals, all of which are capable of damaging most drugs.

Accordingly, there is a need for an improved system and method for aseptic filling of a terminally sterilized drug delivery device so that a terminally sterilized pre-filled device can be provided to the user. The system and method should avoid damage to the drug that can occur with heat, radiation, chemical sterilization techniques, or the like.

SUMMARY

The present disclosure in various embodiments includes systems and methods of packaging for a pre-filled drug delivery device. In an embodiment, a system for sterilizing a drug delivery device may include a drug delivery device that may have a first self-healing seal. The first self-healing seal may be configured to seal a fluid reservoir disposed within the drug delivery device. A sealable container may be for receiving the drug delivery device therein. The sealable container may have a base portion and/or may have a cover portion. A second self-healing seal may be disposed on the cover portion. The second self-healing seal may be positioned to substantially align with the first self-healing seal when the drug delivery device is disposed within the sealable container. A fill receiver may include a fill path. The fill path may be configured to pass through the first and second self-healing seals to fluidly couple the fill receiver to the reservoir of the drug delivery device. The fill receiver may include at least one sealing protrusion on an inner surface of the fill receiver. The fill receiver may include a one-way valve. The valve may be configured for flow in a direction toward the reservoir. At least one of the first self-healing seal and the second self-healing seal may comprise silicone. An alignment ring may be disposed on the cover portion between the first self-healing seal and the second self-healing seal and may be about the first self-healing seal. The base portion of the sealable container may be configured to position the device such that the first self-healing seal is substantially aligned with the second self-healing seal. A tub may be configured to contain the drug delivery device and the sealable container for sterilizing the system. The tub may be configured to position the drug delivery device for filling the fluid reservoir with a drug. The cover portion may be gas permeable. A plunger may be within the fluid reservoir and may be in a position controlling a volume of a fluid within the reservoir. Insulin may be disposed within the fluid reservoir. The first and second self-healing seals may be configured for a fill path to reversibly translate into the first and second self-healing seals to fluidly couple the fill path to the fluid reservoir such that a sterility of the device may be maintained and a fluid may not pass through the first and second self-healing seals. The cover portion may be removably adhered to the base portion. The first self-healing seal may abut the second self-healing seal.

In an aspect, a method for sterilizing a drug delivery device may include disposing a drug delivery device within a sealed container. The drug delivery device may have an empty reservoir. A fill path may be coupled to the reservoir by disposing the fill path through a first self-healing seal in the drug delivery device and through a second self-healing seal in a cover portion of the sealed container. The drug delivery device, the sealed container, and the fill path may be disposed in a tub. The drug delivery devices, sealed containers, and fill path may be subjected to terminal sterilization. The tub may be placed into an aseptic environment. A fill nozzle of a liquid drug dispensing system may be interfaced with the fill path of the drug delivery device. A liquid drug may be supplied into the reservoir. The fill path from the drug delivery device may be disengaged by removing the fill path from the first and second self-healing seals. The first self-healing seal may be aligned with the second self-healing seal. A plurality of assemblies comprising the drug delivery device, the sealed container, and the fill path may be arranged in the tub. The tub may be sealed. The tube may be unsealed. The drug delivery devices, sealed containers, and fill path may be subjected to terminal sterilization comprising ethylene oxide.

In an aspect, a device may include a housing. A fluid reservoir may be disposed within the housing. A fill port may be disposed on the housing. A first self-healing seal may be disposed within the fill port and may be configured to seal the fluid reservoir and substantially align with a second self-healing seal disposed on a container. The first and second self-healing seals may be configured for a fill path to reversibly translate into the first and second self-healing seals that may fluidly couple the fluid path to the fluid reservoir such that a sterility of the device may be maintained and a fluid cannot pass through the first and second self-healing seals. The first self-healing seal may comprise silicone.

BRIEF DESCRIPTION OF THE DRAWINGS

Non-limiting embodiments of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment shown where illustration is not necessary to allow those of ordinary skill in the art to understand the disclosure. In the figures.

DETAILED DESCRIPTION

The present disclosure is not limited to the particular embodiments described. The terminology used herein is for the purpose of describing particular embodiments only and is not intended to be limiting. Unless otherwise defined, all technical terms used herein have the same meaning as commonly understood by one of ordinary skill in the art to which the disclosure belongs.

As used herein, the singular forms "a," "an," and "the" are intended to include the plural forms as well, unless the context clearly indicates otherwise. The terms "comprises" and/or "comprising," or "includes" and/or "including" when used herein, specify the presence of stated features, regions, steps elements and/or components, but do not preclude the presence or addition of one or more other features, regions, integers, steps, operations, elements, components and/or groups thereof.

As used herein, the conjunction "and" includes each of the structures, components, features, or the like, which are so conjoined, unless the context clearly indicates otherwise, and the conjunction "or" includes one or the others of the structures, components, features, or the like, which are so conjoined, singly and in any combination and number, unless the context clearly indicates otherwise.

All numeric values are herein assumed to be modified by the term "about," whether or not explicitly indicated. The term "about", in the context of numeric values, generally refers to a range of numbers that one of skill in the art would consider equivalent to the recited value (i.e., having the same function or result). In many instances, the term "about" may include numbers that are rounded to the nearest significant figure. Other uses of the term "about" (i.e., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g. 1 to 5 includes 1, 1.5, 2, 2.75, 3, 3.80, 4, and 5).

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to affect such feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

This disclosure presents various systems, components, and methods related to drug delivery devices. Each of the systems, components, and methods disclosed herein provides one or more advantages over conventional systems, components, and methods.

The disclosed devices, systems and methods address issues relating to device sterilization and providing a device that is pre-filled with a liquid drug. The disclosed devices, systems, and methods facilitate aseptic filling of a terminally sterilized drug delivery device, resulting in a terminally sterilized pre-filled device. As mentioned, one problem with providing a pre-filled drug delivery device is that it can be difficult or impossible to sterilize the pre-filled device without damaging or otherwise disturbing the liquid drug, because conventional sterilization processes may require heat, radiation, or chemicals all of which are capable of damaging most drugs.

The disclosed systems and methods enable a terminally sterilized drug delivery device to be filled after it has been sterilized, and while it remains in its sterile packaging. By filling the drug delivery device through the sterile packaging, it is possible to provide a terminally sterilized device pre-filled to the user.

Advantages of the disclosed systems and methods may include allowing for sterilization of the drug delivery device without the drug being present in the device, allowing a pre-filled device to be provided to the user, thereby improving the user experience and reducing user steps, among others.

Figure 1:
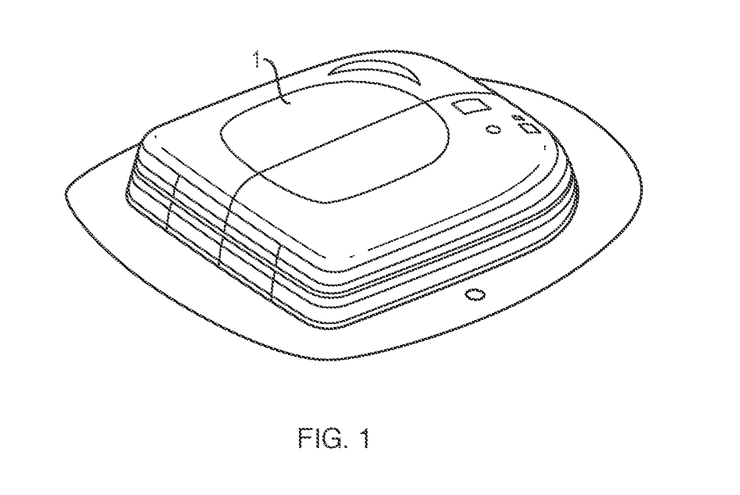
FIG. 1 illustrates an isometric view of a drug delivery device, in accordance with an embodiment of the present disclosure.
Figure 2:
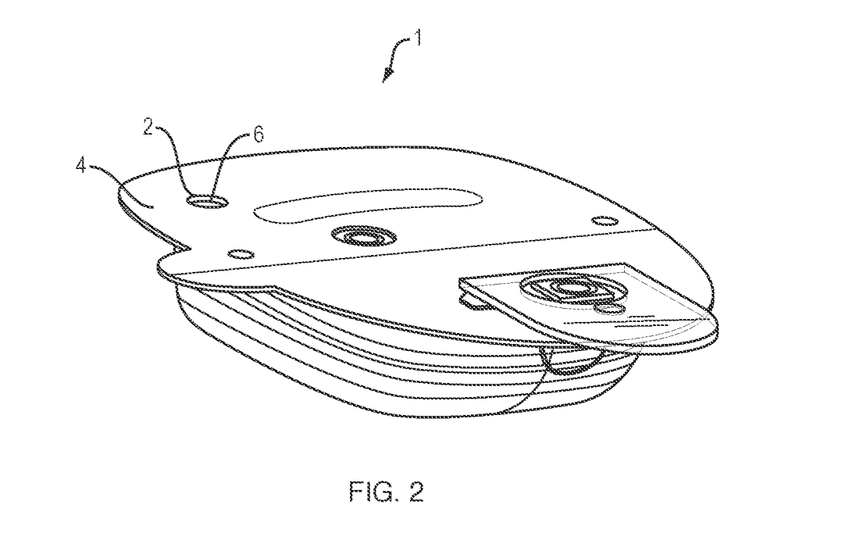
FIG. 2 illustrates a reverse isometric view of the drug delivery device of FIG. 1.

With reference to FIG. 1, an embodiment of a drug delivery device 1 according to the present disclosure is illustrated, which in some embodiments can be an Omni-Pod® (Insulet Corporation, Billerica, Mass.) insulin delivery device. The device 1 includes a liquid drug reservoir (not shown) within a housing. FIG. 2 shows the location of a fill port 2 on an undersurface 4 of the drug delivery device 1. The location of the fill port 2 is such that an axis perpendicular to a plane created by the fill port 2 is substantially directed to a fluid reservoir (not shown) within the housing of the device 1. It will be appreciated that the fill port 2 can include a first self-healing seal 6 along its axis such as a silicone disc or other appropriate seal. The first self-healing seal 6 is configured to seal the reservoir. The fill port 2 can be fluidly coupled to the reservoir disposed within the drug delivery device 1. Any of the fluid arrangements, including any of the drug delivery systems disclosed herein, can be part of a wearable or on-body drug delivery device or pump, such as an OmniPod® (Insulet Corporation, Billerica, Mass. USA) device and/or any of the drug delivery devices described in U.S. Pat. Nos. 7,303,549; 7,144,384; 7,137,964; 6,960,192; 6,740,059; 6,699,218; 9,402,950; 7,771,412; 7,029,455; 6,740,05; and 6,656,159, each of which is incorporated herein by reference in its entirety and for all purposes.

In various embodiments described here or otherwise within the scope of the present disclosure, a self-healing seal may comprise silicone, other vulcanized rubbers, polyurethane, or the like. Such self-healing seals may be reversibly pierced by an object (e.g., with a needle), and remain sealed after removal of the piercing object. These seals may maintain a sterility barrier even after a traumatic piercing, puncturing, or the like. The aperture left behind in the seal at the piercing site is small enough that a microbe cannot make its way through. The compressional forces within the seal onto itself leaves no air gap at the piercing site once the piercing object is removed.

Figure 3:
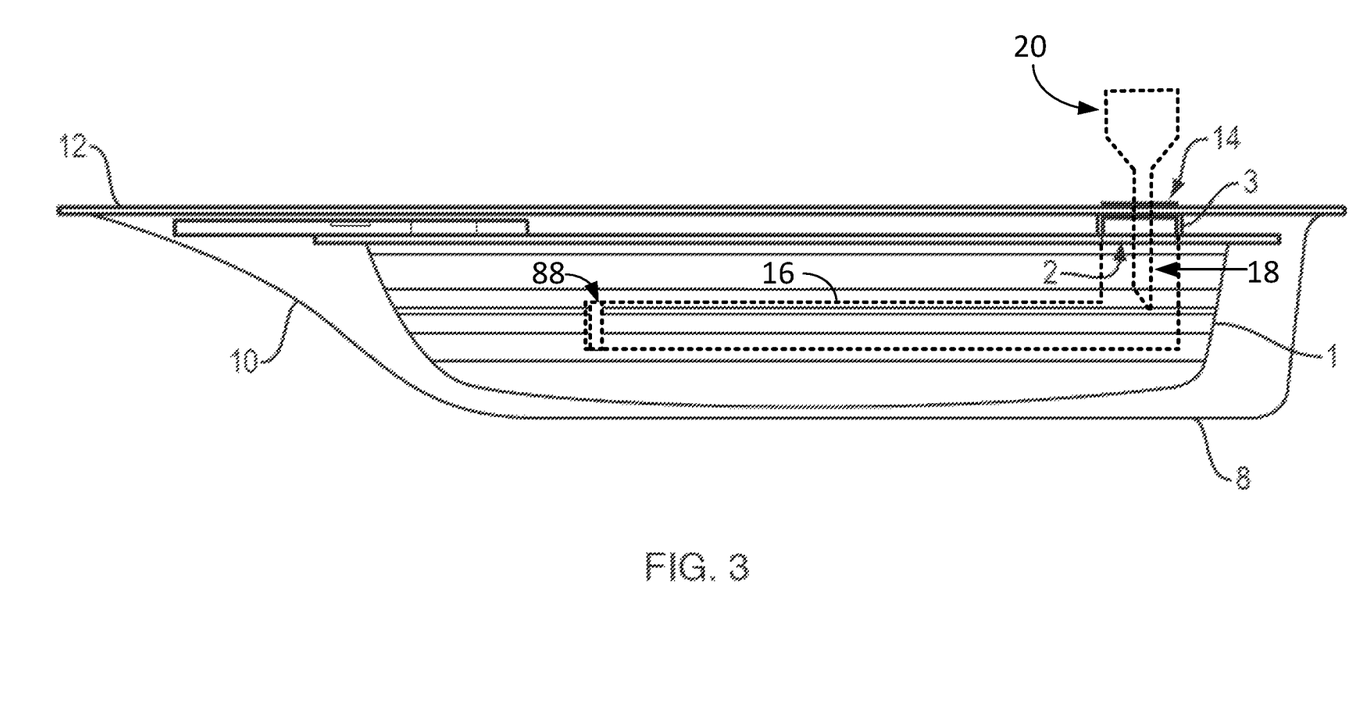
FIG. 3 illustrates a side view of a drug delivery system including the device of FIG. 1 disposed in a sealed container, in accordance with an embodiment of the present disclosure.
Figure 4:
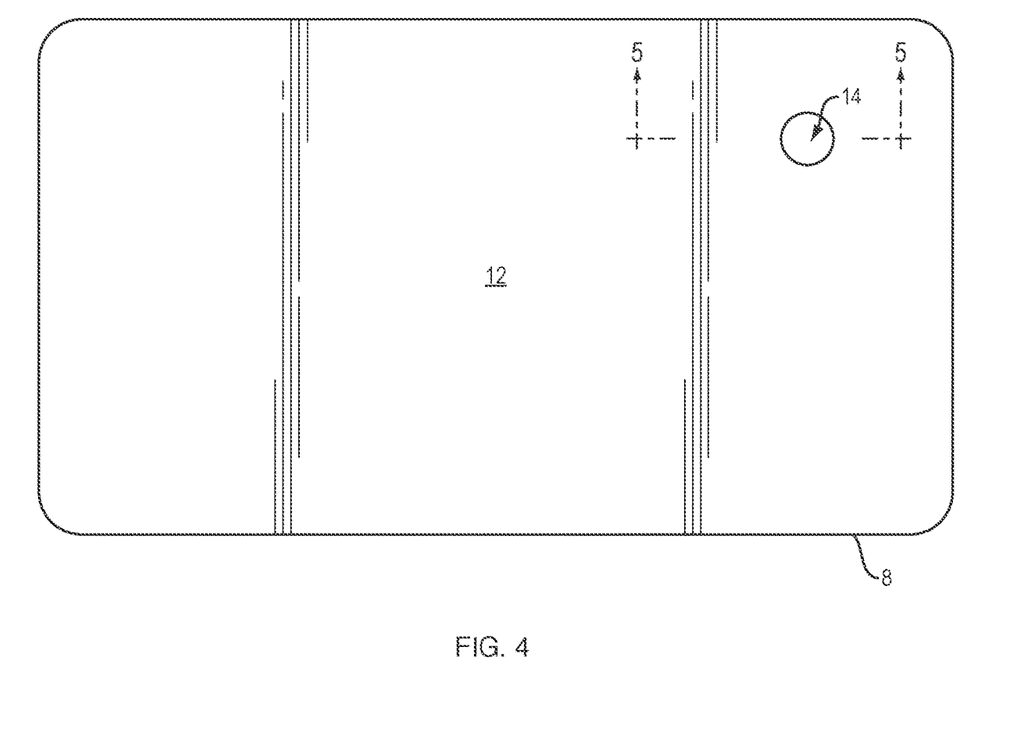
FIG. 4 illustrates a bottom view of the sealed container and drug delivery system of FIG. 3.

With reference to FIG. 3, a side view of an embodiment of a drug delivery system according to the present disclosure is illustrated with a device 1 within a sealed container 8, e.g. a blister pack. The drug delivery device 1 is sealed within the sealed container 8, which includes a base portion 10, that may be plastic, and a removable cover portion 12. In this configuration, the drug delivery device 1 and sealed container 8 have yet to be sterilized. Because the device 1 and container 8 have yet to be sterilized, there is no liquid drug in the device 1. The removable cover portion 12 may include a second self-healing seal 14 which can be positioned substantially aligned with the fill port 2 of the drug delivery device 1. An alignment ring 3 may be disposed on a surface of the cover portion 12 that is facing the device 1 and interior of the base portion 8. The alignment ring 3 is disposed between the first self-healing seal 2 and the second self-healing seal 14 and may be positioned about the first self-healing seal 2 and/or the second self-healing seal 14. The alignment ring 3 may include geometry that substantially aligns the first self-healing seal 2 with the second self-healing seal 14. For example, the alignment ring 3 may be adhered to the cover portion 12 and include a circular lip that acts as a border around the first self-healing seal 2 such that the first and second self-healing seals 2 and 14 substantially align. The alignment ring 3 may instead, for example, be adhered to the underside of the device 1 and about the first self-healing seal 2 and may include geometry that holds the second self-healing seal 14 substantially aligned with the first self-healing seal 2. FIG. 4 illustrates a top view of the sealed container 8 showing the position of the second self-healing seal 14 within the cover portion 12. While FIGS. 3 and 4 illustrate the seals 2 and 14 aligned with/through the cover 12, in various embodiments the seals 2 and 14 may instead be aligned with/through the base portion 10. For example, the device 1 and packaging (e.g., base portion 10 and cover 12) may be positioned on an edge of the base portion 10, and the seals 2 and 14 may be aligned with/through a side of the base portion rather than through the cover 12. Such positioning of the device 1 and packaging may allow for efficient packaging in a sterility tub.

In various embodiments described here or otherwise within the scope of the present disclosure, a removable cover portion of a sealed container may be gas permeable, but not permeable to microbes, spores, and the like such that an aseptic barrier is maintained. Such materials for the removable cover portion may include polyurethane or the like. A cover portion may be welded or otherwise adhered to a base portion to form a container. The cover portion may seal a device within a container while the container and the contained device are subjected to sterilization. Should the container be subjected to a non-sterile atmosphere, the contained device will remain sterile.

Figure 5:
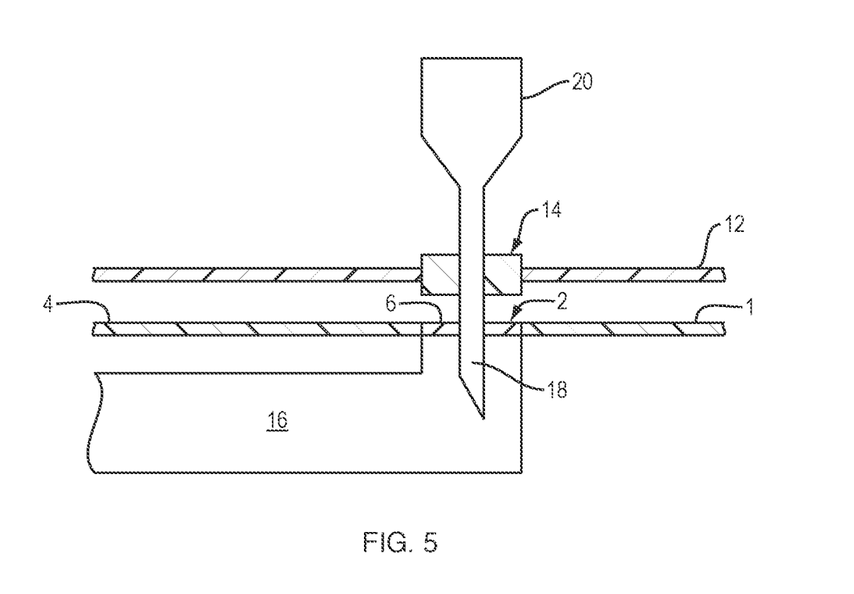
FIG. 5 illustrates a cross-section view, taken along line 5-5 of FIG. 4 including a fill receiver, in accordance with an embodiment of the present disclosure.

With reference to FIG. 5, an illustrated partial cross-section view of an embodiment of a drug delivery device 1 according to the present disclosure is within the sealed container including the cover portion 12. This illustration is an example alignment of the second self-healing seal 14 with the fill port 2 and the first self-healing seal 6. In this view, the fill port 2 is fluidly coupled to a fluid reservoir 16 disposed within the drug delivery device 1. A fill path 18 of a fill receiver 20 (not illustrated in FIG. 4) is illustrated in the fill position such that the needle portion 21 has pierced the first and second self-healing seals 6 and 14 and is in fluid communication with the reservoir 16. In some embodiments, the fill path 18 comprises a filling needle. The fill receiver 20 and fill path 18 may reversibly translate into the first and second self-healing seals 6 and 14 to fluidly couple the fluid path 18 to the reservoir 16 such that sterility of the device 1 is maintained and a fluid cannot pass through the first and second self-healing seals 6 and 14. In various embodiments, the self-healing seals 6 and 14 may abut each other and may be adhered to each other.

In the illustrated position of FIG. 5, the contained device 1, cover portion 12, and fill receiver 20 are ready for sterilization. In this position, the desired sterilization medium may flow about and through the permeable cover portion 12 and into and about the device 1. The sterilization medium may also flow about and through the fill receiver 20 and fill path 18 and into the reservoir 16. The result of sterilizing the components of FIG. 5 in this position is a device 1, packaging (including the cover 12 and base portion of a container (not shown)), fill receiver 20, and reservoir 16 that are all sterilized and ready to receive a liquid drug (e.g., insulin).

In the illustrated position of FIG. 5, the sterilized fill receiver 20 and fluid reservoir 16 are ready for filling. A desired amount of liquid drug may be supplied (e.g., pumped) into the reservoir 16 via the fill path 18 of the fill receiver 20. Once filling is complete the fill path 18 can be withdrawn, and the first and second self-healing seals 6, 14 re-seal, maintaining the sterility of the device 1 and the interior of the sealed container 8.

Figure 6:
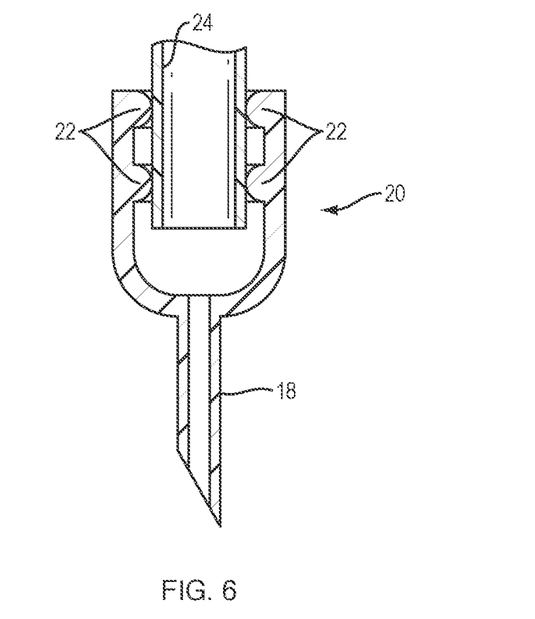
FIGS. 6 and 7 illustrate cross-section views of exemplary fill receivers for use in filling the drug delivery device of FIG. 1, in accordance with embodiments of the present disclosure.
Figure 7:
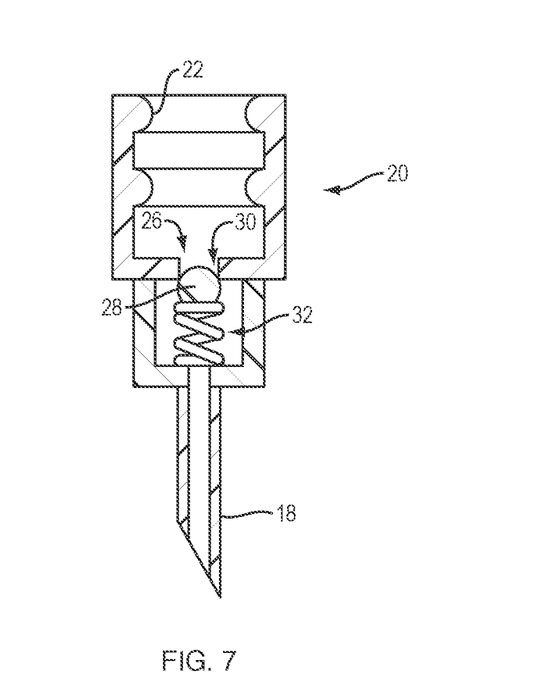

With reference to FIGS. 6 and 7, cross-section views of embodiments of exemplary fill receivers 20 according to the present disclosure are illustrated. The fill receiver 20 of FIG. 6 includes multiple sealing protrusions 22 disposed on an inner surface thereof for sealing against an outer surface of a fill nozzle 24 of a liquid drug dispensing system (not shown). The sealing protrusions 22 may be compressible to accommodate and provide a tight fit with the fill nozzle. The sealing protrusions 22 may instead be, e.g., O-rings or the like. Although not shown, it will be appreciated that the fill nozzle 24 may be coupled to a programmable robot which may position the fill nozzle 24 in substantial alignment with the fill receiver 20 of one or more drug delivery devices. The fill receiver 20 of FIG. 7 includes the aforementioned sealing protrusions 22 on an inner surface thereof for sealing against a fill nozzle (not shown in FIG. 7) of a fill station. The fill receiver 20 of this embodiment further includes a one-way valve 26. In the illustrated embodiment, the one-way valve 26 includes a ball 28 for sealing an opening 30 of the fill receiver 20. The ball 28 is pressed into engagement with a seat surrounding the opening 30 by a spring 32. As will be appreciated, the one-way valve 26 may allow fluid to flow through the fill receiver 20 into the fill path 18 (by forcing the ball downward, out of engagement with the seat), but will prevent fluid from flowing in the reverse direction. It will be appreciated that any other appropriate one-way valve could be used in lieu of a ball valve.

Figure 8:
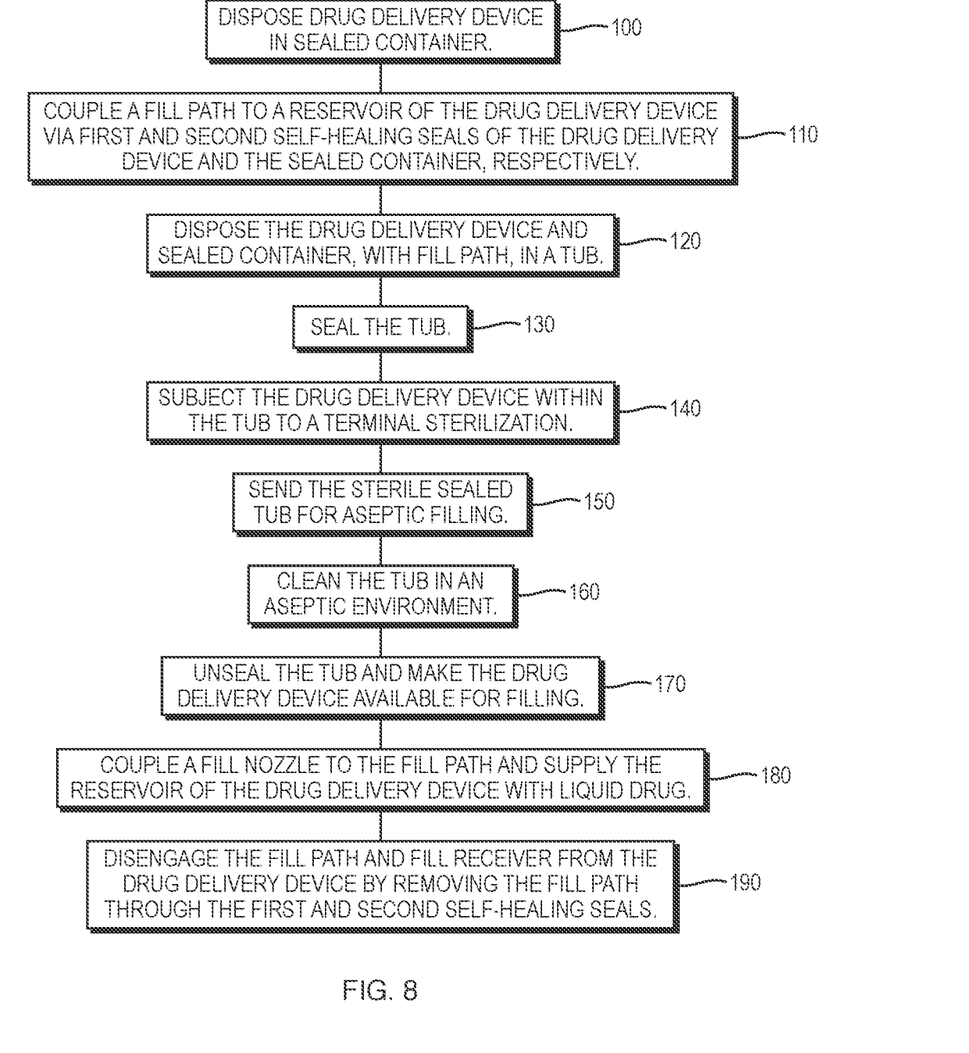
FIG. 8 illustrates a flow diagram of a method, in accordance with an embodiment of the present disclosure.

With reference to FIG. 8, an embodiment of a method according to the present disclosure is illustrated. At step 100, the fluid reservoir 16 of a drug delivery device 1 is in an empty configuration (i.e., no liquid drug is present), and the drug delivery device 1 is disposed within a sealed container 8. A first self-healing seal 6 of the device 1 may be aligned with a second self-healing seal 14 of the container 8. At step 110, a fill path 18 is fluidly coupled to the reservoir 16 of the drug delivery device 1. The fill path 18 may be disposed through a first self-healing seal 6 and a fill port 2 in the drug delivery device 1 and through a second self-healing seal 14 in the cover portion 12 of the sealed container 8. The fill path 18 may be part of a fill receiver 20. The fill receiver 20 may be configured to interface with a fill nozzle (not shown) for receiving liquid drug therefrom. In some embodiments, the fill receiver 20 includes a one-way valve 26 for sealing the fill path 18 after the reservoir 16 has been filled with liquid drug.

At step 120, the drug delivery device 1, coupled with the fill path 18 of the fill receiver 20, is placed into a tub. In some embodiments, multiple sealed devices 1 with associated fill paths 18, fill receivers 20, and containers 8 can be placed into a single tub to be sterilized together. Multiple assemblies of the devices 1, containers 8, fill paths 18, and fill receivers 20 may be arranged in the tub with spacing and positioning for sterilization and filling. At step 130, the tub is sealed. At step 140, the drug delivery devices 1 within the tub are subjected to terminal sterilization (e.g., ethylene oxide (EO), steam, gamma radiation, or the like). At step 150, the sterile sealed tub is sent for aseptic filling. In some embodiments, the same environments and equipment used for aseptic filling of cartridges and vials is used to aseptically fill the drug delivery device(s) 1.

At step 160, the tub enters an aseptic environment and is cleaned. At step 170 the tub is unsealed and the drug delivery devices 1 therein are made available for filling. The drug delivery devices 1 may be arranged in a known and locatable manner within the tub such that a robot arm coupled to a fill nozzle 24 can be programed and/or operated to easily locate a fill path (i.e., second self-healing seal 14, fill port 2, and/or fill path 18) of each drug delivery device 1 in the tub.

At step 180 the fill nozzle 24 interfaces with the fill path 18 of a targeted drug delivery device 1 and supplies fluid (drug) into the empty fluid reservoir 16 of the device 1. A plunger 88 of the reservoir 16 moves as fluid is supplied to the reservoir 16 to a filled position. The plunger 88 may vary its position to control a volume of a fluid within the reservoir 16. It will be appreciated that the position will be variable based on a desired fill volume.

At step 190 filling is complete and the fill receiver 20 (including fill path 18) is disengaged from the drug delivery device 1 by removing (e.g., pulling) the fill path 18 through the first and second self-healing seals 6 and 14. Removing the fill path 18 through the first and second self-healing seals 6 and 14 will not compromise the integrity of the sealed container 8 or the device 1. The result is a pre-filled, sterilized drug delivery device 1 in its sterile packaging (sealed container 8).

Certain embodiments of the present disclosure are described herein. It is, however, expressly noted that the present disclosure is not limited to these embodiments, but rather the intention is that additions and modifications to what is expressly described herein are also included within the scope of the disclosure. Moreover, it is to be understood that the features of the various embodiments described herein are not mutually exclusive and can exist in various combinations and permutations, even if such combinations or permutations are not made expressly herein, without departing from the spirit and scope of the disclosure. In fact, variations, modifications, and other implementations of what is described herein will occur to those of ordinary skill in the art without departing from the spirit and the scope of the disclosure. As such, the disclosure is not to be defined only by the illustrative description.

What is claimed is:

1. A method comprising:
providing a drug delivery device within a sealable container, the drug delivery device having an empty reservoir and a first self-healing seal;
coupling a fill path to the reservoir by disposing the fill path through the first self-healing seal in the drug delivery device and through a second self-healing seal in the sealable container;
interfacing a fill nozzle of a liquid drug dispensing system with the fill path coupled to the reservoir; and
supplying, via the fill nozzle and the fill path, a liquid drug into the reservoir of the drug delivery device.

2. The method of claim 1, further comprising:
disengaging the fill path from the drug delivery device by removing the fill path from the first self-healing seal and the second self-healing seal.

3. The method of claim 1, further comprising:
aligning the first self-healing seal with the second self-healing seal.

4. The method of claim 1, further comprising:
applying ethylene oxide, steam or gamma radiation to the drug delivery device, sealable container, and fill path.

5. The method of claim 1, further comprising:
prior to providing the delivery device within the sealable container, positioning the first self-healing seal of the delivery device in substantial alignment with the second self-healing seal of the sealable container.

6. The method of claim 1, further comprising:
prior to providing the delivery device within the sealable container, positioning an alignment ring between the first self-healing seal and the second self-healing seal, wherein the alignment ring is configured to substantially align the first self-healing seal in the delivery device with the second self-healing seal.

7. The method of claim 1, further comprising:
sealing the fill path by utilizing a one-way valve within a fill receiver.

8. The method of claim 1, further comprising:
arranging the drug delivery device, the sealable container, and the fill path in an assembly for placement in a tub;
arranging other drug delivery devices, other sealable containers, and other fill paths in respective other assemblies for placement in the tub; and
placing the assembly and the respective other assemblies in the tub.

9. The method of claim 8, further comprising:
subjecting the drug delivery device, the sealable container, and the fill path to terminal sterilization, wherein the terminal sterilization includes sterilizing the assembly and the respective other assemblies in the tub.

10. The method of claim 1, wherein interfacing the fill nozzle of the liquid drug dispensing system with the fill path of the drug delivery device comprises:
sealing an outer surface of the fill nozzle with a sealing protrusion on an inner surface of a fill receiver of the fill path.

11. The method of claim 10, wherein interfacing the fill nozzle of the liquid drug dispensing system with the fill path of the drug delivery device further comprises:

providing a one-way valve in the fill receiver that enables the liquid drug to be provided to the reservoir but prevents the liquid drug from flowing out of the reservoir into the fill receiver.

12. The method of claim 11, wherein enabling the liquid drug to be provided to the reservoir comprises:
opening the one-way valve by forcing a ball in the one-way valve downward out of engagement with a seat within the one-way valve.

13. The method of claim 1, wherein coupling the fill path to the reservoir comprises:
establishing a fluid coupling between the fill nozzle and the reservoir.

14. The method of claim 1, further comprising:
sealing the sealable container by adhering a removable cover to a base portion of the sealable container, wherein the base portion is configured to hold the drug delivery device.

15. The method of claim 1, further comprising:
sealing the sealable container by welding a removable cover to a base portion of the sealable container, wherein the base portion is configured to hold the drug delivery device.

16. The method of claim 1, wherein coupling the fill path to the reservoir comprises:
unsealing the first self-healing seal as the fill path is disposed through the first self-healing seal; and
unsealing the second self-healing seal as the fill path is disposed through the second self-healing seal, wherein a fill receiver of the fill path is in fluid communication with the reservoir.

17. The method of claim 16, further comprising:
upon filling the reservoir, withdrawing the fill path from the first and second self-healing seals;
allowing the second self-healing seal to reseal; and
allowing the first self-healing seal to reseal.

18. The method of claim 9, wherein subjecting the drug delivery device, the sealable container, and the fill path to terminal sterilization comprises:
applying a sterilization medium to a permeable cover portion of the sealable container; and
enabling flow of the sterilization medium about the drug delivery device including into the reservoir via a fill receiver coupled to the fill path.

19. The method of claim 1, wherein sterility of the drug delivery device and liquid drug within the sealable container are maintained after supplying the liquid drug to the reservoir of the drug delivery device.

20. The method of claim 1, further comprising:
disposing the drug delivery device, the sealable container, and the fill path in a tub;
subjecting the drug delivery device, the sealable container, and the fill path to terminal sterilization; and
placing the tub into an aseptic environment.

21. The method of claim 20, further comprising:
sealing the sealable container; and
prior to subjecting the drug delivery device, the sealable container, and the fill path to terminal sterilization, sealing the tub containing the drug delivery device, the sealed sealable container and the fill path.

* * * * *